United States Patent
Pang et al.

(10) Patent No.: US 6,254,539 B1
(45) Date of Patent: Jul. 3, 2001

(54) TRANSDUCER MOTION COMPENSATION IN MEDICAL DIAGNOSTIC ULTRASOUND 3-D IMAGING

(75) Inventors: Linyong Pang, Stanford; John A. Hossack, Palo Alto, both of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/384,074

(22) Filed: Aug. 26, 1999

(51) Int. Cl.[7] .................................................. A61B 8/00
(52) U.S. Cl. ............................................................ 600/443
(58) Field of Search ................................ 600/437, 443, 600/447; 128/916; 73/602

(56) References Cited

U.S. PATENT DOCUMENTS

| | | | |
|---|---|---|---|
| 5,474,073 | 12/1995 | Schwartz et al. | |
| 5,575,286 | 11/1996 | Weng et al. | 600/444 |
| 5,782,766 | 7/1998 | Weng et al. | 600/443 |
| 5,873,830 | 2/1999 | Hossack et al. | 600/447 |
| 5,876,342 * | 3/1999 | Chen et al. | 600/443 |
| 5,899,861 | 5/1999 | Friemel et al. | 600/445 |
| 5,910,114 | 6/1999 | Nock et al. | 600/437 |
| 6,059,727 * | 5/2000 | Fowlkes et al. | 600/443 |
| 6,117,081 * | 9/2000 | Jago et al. | 600/443 |

OTHER PUBLICATIONS

McCann et al., *Multidimensional Ultrasonic Imaging for Cardiology*, Proceedings Of The IEEE, vol. 76, No. 9, Sep. 1998, pp. 1063–1072.

* cited by examiner

Primary Examiner—Francis J. Jaworski
(74) Attorney, Agent, or Firm—Brinks Hofer Gilson & Lione (57) ABSTRACT

A 3-D medical diagnostic ultrasonic imaging system corrects the elevational position of individual pixels based on the elevational motion of the transducer probe and the azimuthal position of individual pixels. In this way, the correct spatial position and orientation of multi-frame, sequentially required images is obtained, and 3-D volume reconstruction is made more accurate. Optionally, the acquired images and the measure of transducer in-plane translation and rotation are also corrected for azimuthal motion of the transducer.

5 Claims, 5 Drawing Sheets

TRANSDUCER MOTION COMPENSATION IN MEDICAL DIAGNOSTIC ULTRASOUND 3-D IMAGING

BACKGROUND

This invention is related to medical ultrasonic diagnostic imaging, and more specifically to methods that register multiple ultrasonic image frames in a 3-D spatial model.

When an ultrasound transducer is moved along a patient's body, multiple image frames (e.g., B-mode image frames) can be acquired sequentially. The spatial coordinates of each image frame can be determined using any of various prior-art approaches. For example, image correlation methods can be used to develop frame coordinates in the frame of reference of the imaged tissue. See, for example, U.S. patent application Ser. Nos. 08/621,561, 08/807,998, and 08/916,585, all assigned to the assignee of the present invention. Other well-known approaches for determining frame coordinates include image decorrelation methods (Friemel, et al U.S. Pat. No. 5,899,861) mechanical positioning devices for the transducer (McCann, et al. "Multidimensional Ultrasonic Imaging for Cardiology" (Proc. of IEEE, 76, 9, pp 1063–1072, September, 1988) and magnetic or other sensors for locating the transducer in space (Schwartz U.S. Pat. No. 5,474,073). Once the ultrasonic image frames and the frame coordinates have been obtained, the frames can be registered in a 3-D spatial model.

Conventional systems as described above exhibit systematic errors in the 3-D spatial model due to the fact that the transducer is in motion as the image frames are acquired, and each frame includes data acquired over a large number of separate ultrasound beams that are fired sequentially in time. A need presently exists for an improved approach that reduces such errors.

SUMMARY

By way of introduction, the preferred embodiments described below correct the spatial coordinates of medical diagnostic ultrasound images in a 3-D system. Transducer motion is determined at least in the elevational direction, and then the elevational positions of individual pixels of the image are corrected as a function of both the transducer elevational motion and the azimuthal position of the respective pixels.

The foregoing paragraph has been provided by way of introduction and is not intended to limit the scope of the following claims.

DETAILED DESCRIPTION OF THE PRESENTLY PREFERRED EMBODIMENTS

A. General Discussion

1. Elevational Transducer Motion Distortion

Figures 1, 2:
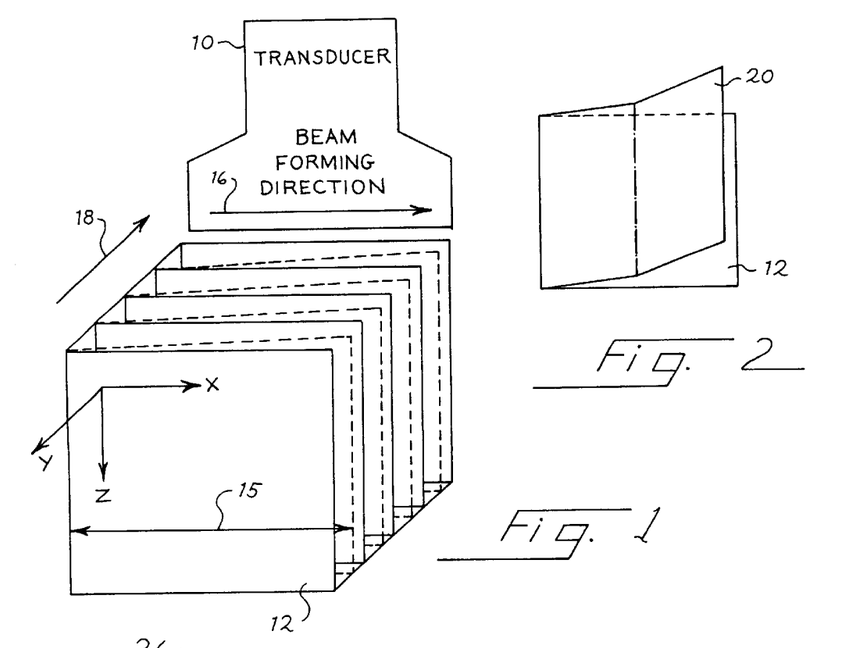
FIGS. 1 and 2 are schematic representations showing elevational position errors in 3-D spatial models.

FIG. 1 illustrates an example of how elevational transducer motion (perpendicular to the image plane) causes the image planes to be skewed in the elevational direction. In FIG. 1, an ultrasonic transducer array is indicated at 10, and the transducer array 10 is moved in the elevational direction as indicated by the arrow 18 to acquire a series of acquired frames 12. In this example, each frame 12 is acquired from a series of consecutively fired ultrasound beams, and these beams are formed from left to right within the frame, as indicated by the scanning direction arrow 16. Using the coordinate system illustrated in FIG. 1 (a local coordinate system in the frame of reference of the transducer array), the scanning direction is aligned with the azimuthal axis X and the transducer motion is aligned with the elevational axis Y. The example of FIG. 1 considers a linear transducer array 10. In this example, W is the width of an image frame obtained by keeping the transducer array 10 stationary. A sign function is defined as follows:

$$\text{sign} = \begin{cases} +1, \text{ if transducer array scans from left to right} \\ -1, \text{ if transducer array scans from right to left.} \end{cases} \quad (1.1)$$

Thus, the sign function has the value +1 for the example of FIG. 1. As the transducer array is moved along the elevation direction to acquire the acquired frames 12, the global position and orientation of each frame are obtained from a conventional 3-D positioning module. As explained above, such a module can include a transducer position sensor of any suitable type, or alternately the global position and orientation of individual frames can be computed using image correlation/decorrelation techniques. See, for example, the techniques disclosed in U.S. patent application Ser. No. 08/916,585 and U.S. Pat. No. 5,899,861. Multiple measurements of global position and orientation may be combined to improve the accuracy of a motion estimate. Let $\Delta Y$ be the transducer motion during acquisition of a single frame along the elevational direction estimated by any of these techniques.

The acquired frames and their global orientation are both distorted due to the motion of the transducer array 10 in the elevational direction. In this simple example, the angle between the true image plane of the actual frame 14 and the plane of the transducer array 10 is approximately equal to $$\beta = \frac{\text{sign} \cdot \Delta Y}{W}. \quad (1.2)$$

The true width of an individual frame along the azimuthal direction X (indicated by the arrow 15 in FIG. 1) is therefore equal to $$W_{true} = \frac{W}{\cos\beta}. \quad (1.3)$$

Note that the formula of Equation 1.3 is a first order approximation. When the elevational motion of the transducer array is not a simple, constant velocity motion in the elevation direction, the actual image frame may not lie in a single plane. For example, a motion of one centimeter per second in the elevation direction for the first half of the frame and the motion of 2 centimeters per second for the second half of an image frame will result in an actual frame 20 that is positioned as shown in FIG. 2. When such information is known, it can be used if required. However, this is typically a second order error, and Equation 1.3 is adequate for many practical applications.

2. Azimuthal Transducer Motion Distortion

Figure 3:
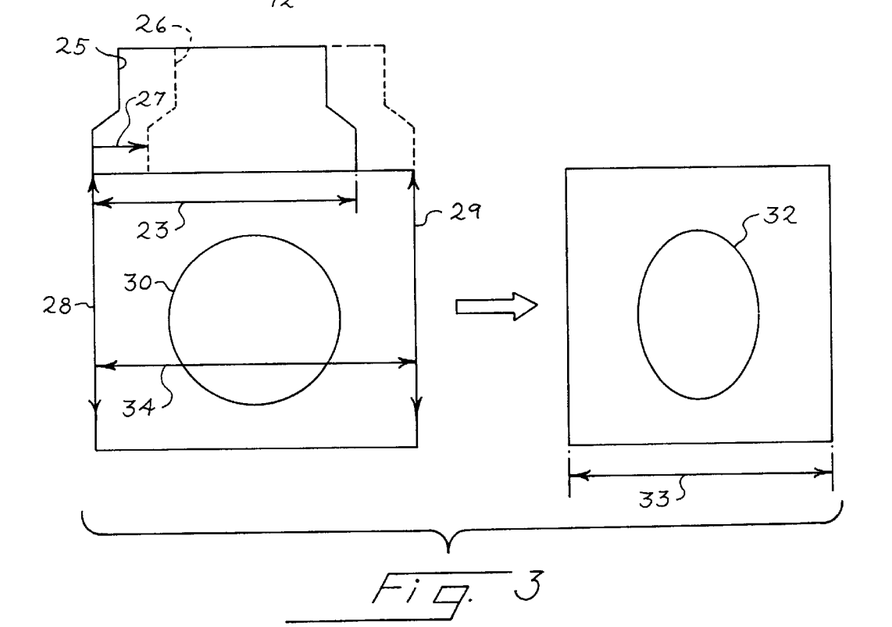
FIG. 3 is a schematic representation showing azimuthal transducer motion distortion.

Transducer motion in the azimuthal direction also causes an image distortion, as shown in FIG. 3. In FIG. 3, the reference symbol 25 is used to designate the transducer array at the start of acquisition of a specific image frame, and the reference symbol 26 is used to indicate the position of the transducer array at the end of the acquisition of this frame. The azimuthal motion of the transducer array between the start and end of the frame is indicated by the vector 27, and this motion corresponds to the actual azimuthal displacement $\Delta X$ discussed below. The image frame shown in FIG. 3 is acquired with multiple scan lines including a first scan line 28 and a last scan line 29. Thus, in this embodiment, the actual frame is acquired using scan lines that progressively move from left to right in the view of FIG. 3. Reference symbol 30 indicates the actual, undistorted shape of a target. The assumed width of the image W is indicated at 33, and this dimension corresponds to the actual width of the image for the case of no azimuthal transducer motion. However, in the case of transducer motion from left to right as shown in FIG. 3, the actual region that is scanned between the initial scan line 28 and the final scan line 29 extends over the width W+$\Delta X$, as shown at 34.

As shown at the left-hand side of FIG. 3, at the time the final scan line 29 is acquired, the transducer array has moved some amount of distance, $\Delta X$ in this example. Since the imaging system typically does not take into account the motion of the transducer array, the width of the acquired images will not account for transducer motion. For this reason, the image size of objects of the acquired image will be the same as the actual size of the object if the transducer array is held motionless on the subject, but they will not be equal if the transducer array is moved in the azimuthal direction. As shown on the right-hand side of FIG. 3, if transducer motion is not corrected, the acquired image shows a distorted image 32 of the target. This is because the acquired image has a width W as shown at 33, instead of the width W+$\Delta X$ as shown at 34.

When tracking arrays are used, as described in above-referenced U.S. patent application Ser. No. 08/916,585, the associated tracking images are subject to transducer motion distortion in the azimuthal planes of the tracking arrays. The distortion correction techniques described herein can be used to correct for such distortion in tracking images. In general, scanning patterns and azimuthal motion will differ between the tracking arrays and the main array, and separate corrections will be preferred.

As discussed below, the transducer motion along the azimuthal direction also distorts the estimate of transducer in-plane rotation.

3. The Recovery of the Actual Azimuthal Transducer Motion from the Acquired Images For simplicity, the following discussion will first consider the case of a linear transducer array. In this discussion, the symbol W is used for the width of an acquired image obtained when the transducer array is maintained in a stationary location with respect to the target. Now the transducer array is moved along a direction with an azimuthal component as described above and a series of images is acquired. Any suitable method is used to determine $\Delta X'$, the apparent displacement or motion in the azimuthal direction between the two acquired images, in the local coordinate frame of the transducer array. For example, the minimum sum of absolute differences method described in U.S. patent application Ser. No. 08/916,585 can be used.

The present inventors have recognized that $\Delta X'$ is inaccurate because the widths of the images acquired by the transducer array are inaccurate due to the transducer motion distortion described in the preceding section. In the following discussion, the term $\Delta X$ will be used for the true or actual, undistorted motion between the two selected images along the azimuthal direction.

The sign function of Equation 1.1 is also applicable here:

$$\text{sign} = \begin{cases} +1, \text{if transducer array scans from left to right} \\ -1, \text{if transducer array scans from right to left} \end{cases} \quad (3.1)$$

The distorted width of the image is equal to W and the true or actual width of the image is equal to W+sign·$\Delta X$, as described above in conjunction with FIG. 3. Thus, the ratio of the true pixel width to the motion-distorted pixel width is given by the following equation:

$$\text{ratio} = \frac{W + \text{sign} \cdot \Delta X}{W}. \quad (3.2)$$

Note that $\Delta X$ is an unknown in this equation, but that $\Delta X'$ can readily be determined by matching or correlating the two selected images.

Since the motions $\Delta X$ and $\Delta X'$ are estimated in units of pixels, $$\frac{\Delta X}{\Delta X'} = \frac{W + \text{sign} \cdot \Delta X}{W}. \quad (3.3)$$

The actual azimuthal motion $\Delta X$ can be obtained by solving equation 3.3:

$$\Delta X = \frac{\Delta X'}{1 - \frac{\Delta X'}{W} \cdot \text{sign}}. \quad (3.4)$$

In equation 3.4, W is known, $\Delta X'$ is estimated, and $\Delta X$ can therefore easily be computed. Note that the above solution is independent of the frame rate and the aperture size.

The solution of equations 3.1–3.4 is well-suited for the case where consecutive frames immediately follow one another, i.e. the frame-to-frame interval is approximately equal to the time between the first and last scan lines of a frame. The methods described in copending U.S. patent application Ser. No. 09/384,707 are preferred for use in the case where the frame-to-frame interval is substantially greater than the time required to acquire an individual frame.

4. Additional Corrections

There are six independent components of motion: three displacements and three rotations. The displacements include the displacement in the azimuthal direction (X), the axial direction (Z), and the elevational direction (Y). We have discussed motion correction for transducer translation in the elevation direction (Y), and the azimuthal direction (X). Translation in the axial direction (Z) usually is very small compared with translation in the azimuthal direction and elevation direction, because the transducer array is moving along the patient's body. For this reason, the error in the axial direction can be ignored. Three rotations include the rotations along the three axes X, Y, and Z. The rotation about the Y axis is the most significant one affected by transducer motion and is preferably corrected. We call this rotation in-plane rotation θ.

Figure 4:
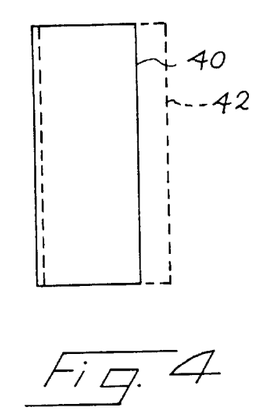
FIGS. 4, 5 and 6 are schematic diagrams showing transducer motion distortion associated with translational and rotational motion of the transducer in the transducer plane.
Figure 5:
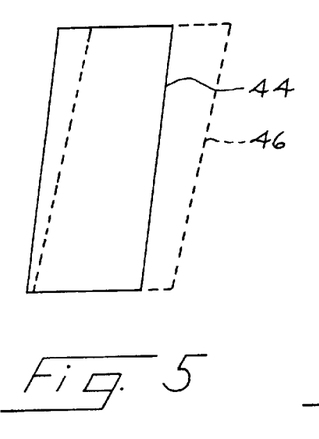
Figure 6:
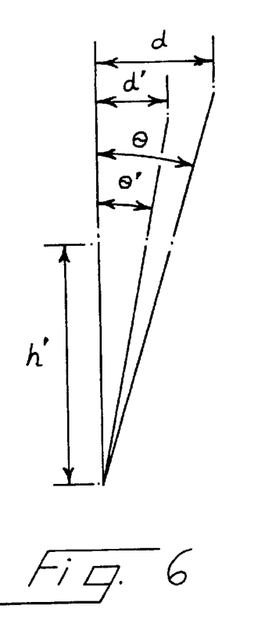

FIG. 4 shows a rectangular image 40 that is motion-distorted due to azimuthal transducer translation, and the dotted lines show the true imaged region 42. FIGS. 5 and 6 illustrate rotation distortion due to rotational motion of the transducer about the Y axis.

In FIG. 5, the imaged region 44 and the actual region 46 are shown when there is significant transducer in-plane rotation. As shown in FIG. 6, the actual in-plane transducer rotation θ is somewhat larger than the motion-distorted estimate of transducer in-plane rotation θ' in this example.

Since the angles of in-plane transducer rotation are typically quite small, they can be approximated by:

$$\theta = \frac{d}{h}. \tag{4.1}$$

The azimuthal offset d at the top of the image is distorted by azimuthal motion of the transducer array. The ratio of the true offset d to the estimated offset d' is equal to the ratio of pixel size distortion:

$$\frac{d}{d'} = \frac{\Delta X}{\Delta X'}. \tag{4.2}$$

As discussed above, image distortion in the axial direction can be ignored for this analysis, and therefore, $$\frac{\theta}{\theta'} = \frac{d}{d'}, \tag{4.3}$$

where θ' and θ are the angle of transducer in-plane rotation before and after the transducer motion error compensation, respectively. Finally, the rotation angle θ' can be corrected by the following approximate formula:

$$\theta = \theta' \frac{\Delta X}{\Delta X'}. \tag{4.4}$$

The motion corrections derived above use a linear transducer array for illustration. In such a linear transducer array, the motion errors for all axial positions are the same. For other types of transducer arrays, the motion errors at different axial positions may be different because the physical width of the B-mode image varies as a function of the axial position.

Figure 7:
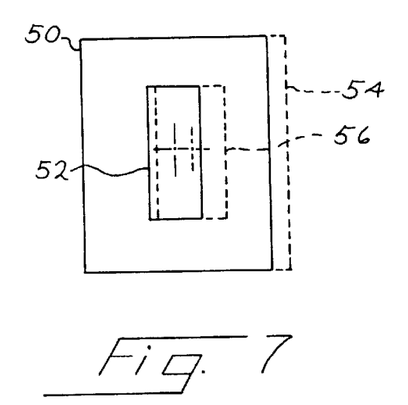
FIGS. 7 and 8 are schematic diagrams illustrating transducer motion correction for linear and curvilinear transducers, respectively, for motion of the transducer in the transducer plane.

As shown in FIG. 7, the image region 50 has a rectangular shape with a linear transducer array, and the azimuthal, translational motion corrections at any axial position are the same. In FIG. 7, the solid lines 50, 52 represent the acquired image and a rectangular box in the acquired image, respectively, when the transducer array is in motion in the azimuthal direction, and the dashed lines 54, 56 illustrate the true shapes of the acquired image 50 and the rectangular box 52, respectively.

Figure 8:
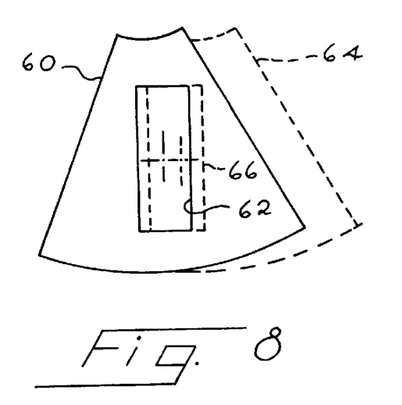

FIG. 8 shows the case for a curvilinear transducer array, where the rectangular shape of the rectangular box is no longer a rectangle in shape in the distorted image. In FIG. 8, reference symbols 60, 62 indicate an acquired image and a rectangular box of the acquired image, respectively, and the dotted line elements 64, 66 represent the actual or true shapes of the elements 60, 62, respectively. The variation of motion distortion as a function of axial position for a curvilinear transducer array is a second order effect, and the motion correction formulas derived above can be used with good results for curvilinear transducers.

For the case where the transducer is not a linear transducer, i.e., Vector™ or curvilinear transducer, the actual image width at different depths is different (as shown in FIG. 8). The motion errors are also different at different depths, because the azimuthal scanning rates are different.

The inplane motion between two images can be characterized by two components: translation of the center of the image, and rotation around the center of the image. The motion compensation formula (Equation 3.4) for translation is still valid for a non-rectangular image, because the apparent translation Δx' and image width W are measured at the center of the image. However, the rotation is affected, and Equation 4.4 is preferably modified when the angle between the left bound and right bound of the image is no longer a small angle.

To obtain the true rotation, let us first consider the apparent translation at the top and bottom of the image, namely $\Delta x_1'$, and $\Delta X_2'$. Using a small angle approximation, we have $$\Delta x_1' = \Delta x' - \frac{h}{2}\theta', \tag{4.5}$$

$$\Delta x_2' = \Delta x' + \frac{h}{2}\theta', \tag{4.6}$$

where h is the height of image, and θ' is the apparent rotation estimated at the center of the image.

Now applying the translation compensation formula (Equation 3.4), we can calculate the true translation at the top and bottom of the image, respectively.

$$\Delta x_1 = \frac{\Delta x_1'}{1 - \frac{\Delta x_1'}{W_1}}, \tag{4.7}$$

$$\Delta x_2 = \frac{\Delta x_2'}{1 - \frac{\Delta x_2'}{W_2}}, \tag{4.8}$$

where $W_1$ and $W_2$ are the width of the image at the top and the bottom when the transducer is held motionless.

Once $\Delta x_1$ and $\Delta x_2$ are known, the true rotation along the center of the image, θ, can be calculated from $\Delta x_1$ and $\Delta x_2$ by the following small angle rotation approximation formula:

$$\theta = \frac{\Delta x_2 - \Delta x_1}{h}. \tag{4.9}$$

Once the motion-distorted estimates of motion ΔX', Δθ' have been corrected as described above to generate the true or actual motion estimates ΔX, Δθ, the size of the images or portions of the images are preferably also corrected. Ignoring second order errors, the image or a portion of an image is scaled by a factor equal to ΔX/ΔX' in the azimuthal direction. This can be conveniently done by scaling azimuthal pixel width by ΔX/ΔX'.

B. Specific Embodiments

Figure 9:
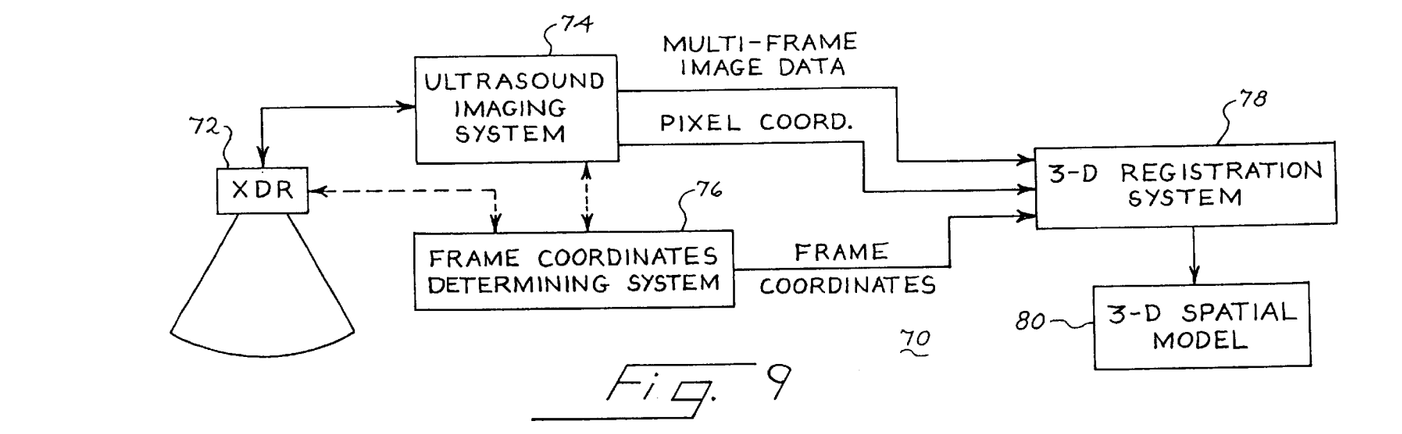
FIG. 9 is a block diagram of an ultrasonic imaging system that incorporates a preferred embodiment of this invention.
Figure 10:
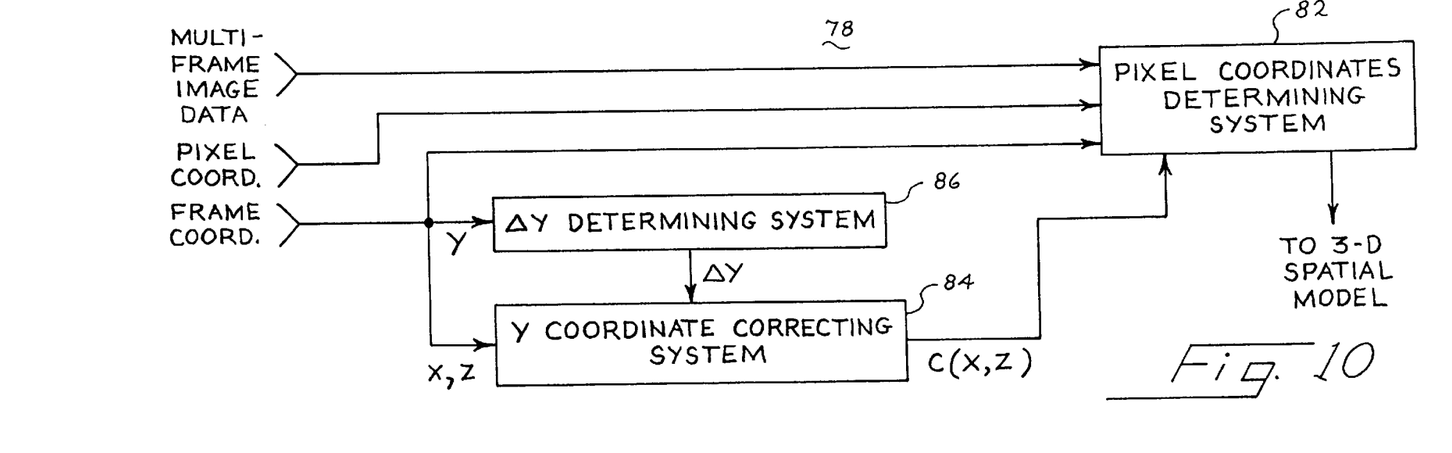
FIG. 10 is a block diagram of the 3-D registration system of FIG. 9.

FIGS. 9 and 10 provide block diagrams of a medical diagnostic ultrasound imaging system that incorporates a preferred embodiment of this invention. The imaging system 70 (FIG. 9) includes an ultrasonic transducer probe 72 that is coupled with an ultrasound imaging system 74. The ultrasound imaging system 74 uses the transducer probe 72 to generate image data and pixel coordinates for individual pixels of acquired frames. The image data can be in any desired imaging mode, such as B-mode imaging (fundamental or harmonic, tissue or agent), color Doppler imaging (velocity, energy, variance, or any combination of these parameters), or the like.

The system 70 also includes a frame coordinates determining system 76 that generates frame coordinates for individual acquired frames of image data. The systems 74, 76, as well as the transducer 72 can take any suitable form. For example, the ultrasound imaging system 74 can include analog or digital beamformers. The transducer probe 72 can include phased array or mechanically steered transducers. One-, 1.5- and 2-dimensional arrays can be used, including both linear and curvilinear arrays. The system 76 can use any desired method for determining frame coordinates. As explained above, image correlation techniques can be used as described in U.S. patent application Ser. Nos. 08/621,561, 08/807,498 and 08/916,585. Alternately, any type of transducer probe positioning system can be used, including articulated mechanical scanning guides (the above-referenced McCann paper), magnetic sensors (U.S. Pat. No. 5,474,073), or time of flight spark sensors.

The image data, the pixel coordinates, and the frame coordinates are applied as an input to a 3-D registration system 78 that is shown in greater detail in FIG. 10. The registration system 78 registers individual image data pixels in 3-D space and stores the pixel values in the appropriate locations of a 3-D spatial model 80.

As shown in FIG. 10, the registration system 78 includes a pixel coordinates determining system 82. System 82 uses the frame coordinates from the system 76, and the image data and the pixel coordinates from the system 74 to generate pixel coordinates for each individual pixel of each acquired frame, using any desired algorithm. Additionally, the registration system 78 includes a Y coordinate correcting system 84 and a $\Delta Y$ determining system 86.

The $\Delta Y$ determining system 86 uses the elevational frame coordinates Y from the coordinate determining system 76 to assess $\Delta Y$, the motion of the transducer probe in the elevational direction. $\Delta Y$ in one example represents the distance traveled by the transducer probe 72 in the elevational direction during the time required to acquire a single frame of image data. Alternately, the motion parameter $\Delta Y$ can be representative of transducer velocity in the elevational direction. The Y coordinate correcting system 84 generates correction values C (x, z) that are used by the system 82 to correct the Y coordinate of individual pixels to account for transducer motion along the elevational direction.

The correction values C (x, z) are determined as a function of both the transducer elevational motion parameter $\Delta Y$ and the azimuthal coordinate X of the individual pixel. The azimuthal coordinate can be the X coordinate of an individual pixel or the scan line number on which an individual pixel was acquired. The azimuthal coordinate of the pixel provides information as to when the pixel was acquired in the frame, and the elevational motion parameter $\Delta Y$ provides information regarding the rate of movement of the transducer probe. The specific function used in the system 84 to generate the correction values C (x, z) can be a linear or nonlinear function, and it can include other parameters. For example, in the case of scan lines that radiate from an apparent point, the correcting system 84 can use both the azimuthal position X and the range position Z of a pixel in combination with the motion parameter $\Delta Y$ to generate C (x, z).

The pixel coordinates determining system 82 generates pixel coordinates in any suitable manner and then corrects the elevational position of individual pixels using the correction values C (x, z) associated with the respective pixels. The pixel coordinates determined in the system 82 are then used to register image data from the system 74 in the 3-D spatial model 80. In this embodiment, the pixel coordinates generated by the imaging system 74 are local coordinates (in the frame of reference of the transducer probe 72), while the frame coordinates generated by the system 76 are global coordinates.

Figure 11:
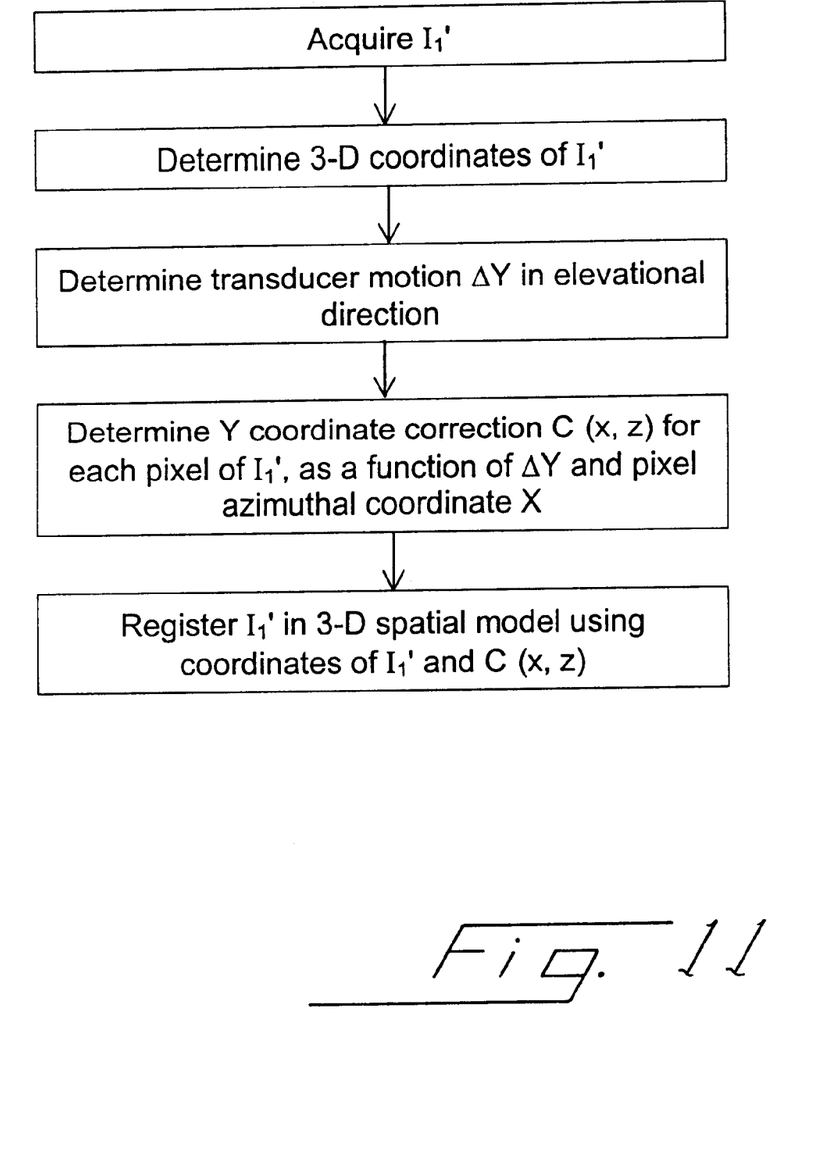
FIG. 11 is a flow chart of a method performed by the system of FIGS. 9 and 10.

FIG. 11 illustrates a method performed by the system 70 described above. In the example of FIG. 11, first an image frame $I_1'$ is acquired and the 3-D coordinates of $I_1'$ are determined. The transducer motion $\Delta Y$ is determined for motion in the elevational direction, and the Y coordinate correction value C (x, z) is determined for each pixel of $I_1'$ as a function of $\Delta Y$ and the pixel azimuthal coordinate X. Finally, the frame $I_1'$ is registered in the 3-D spatial model using the coordinates of $I_1'$ and the correction values C (x, z). The registration methods described in copending U.S. patent application Ser. No. 09/369,824 are preferred. After registration, the image information of the 3-D spatial model can be viewed in any suitable viewing mode, such as a volume rendering, surface rendering, or a 2-D cutting plane that is arbitrarily oriented and positioned.

When a set of image frames is acquired for 3-D imaging, in most cases there is little motion of the transducer probe in the azimuthal direction, because the transducer probe is usually moved along the elevational direction. For this reason, there is often no need to correct the acquired images for distortion caused by azimuthal transducer motion. However, in the event that azimuthal transducer motion distortion is to be corrected, the method of FIG. 12 can be performed at any desired point in the flow chart of FIG. 11.

Figure 12:
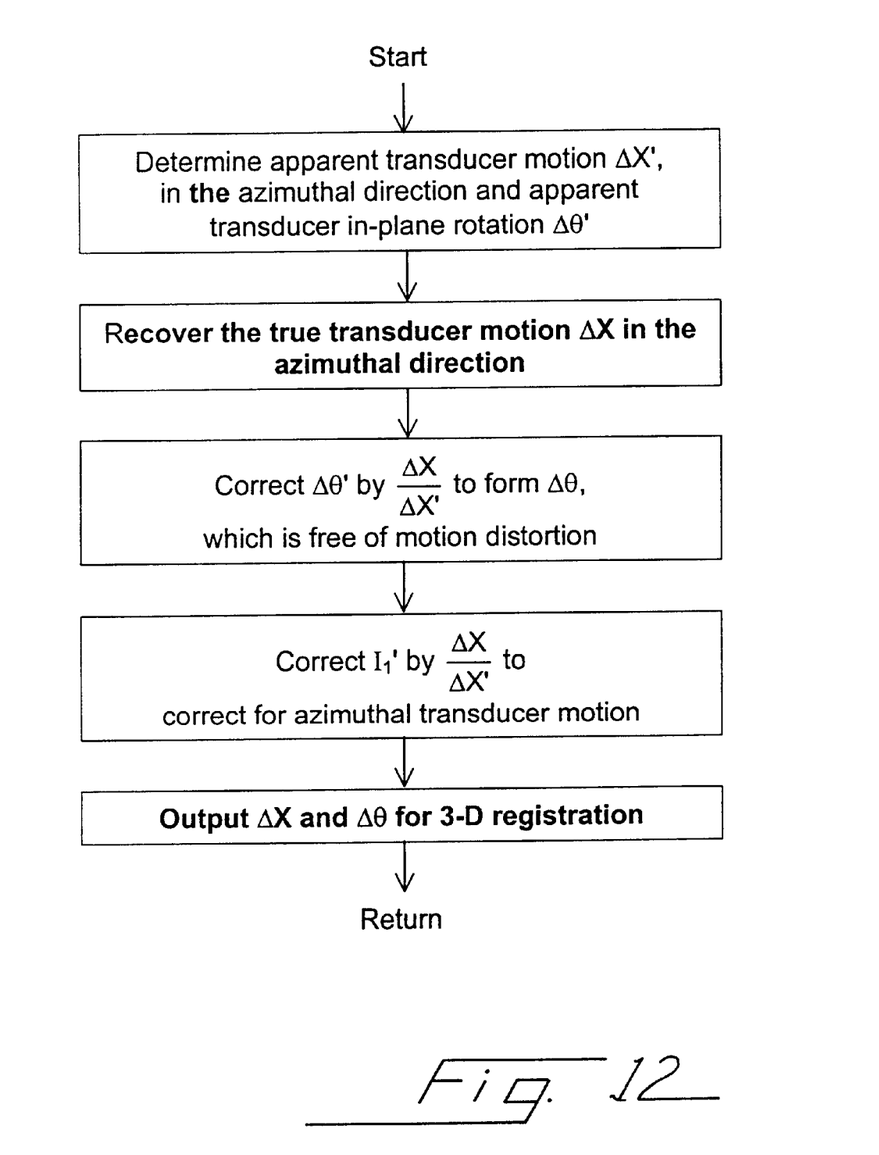
FIG. 12 is a flow chart of a method optionally performed by the system of FIGS. 9 and 10.

In the method of FIG. 12, first the apparent transducer motion $\Delta X'$ in the azimuthal direction and the apparent in-plane rotation $\Delta \theta'$ are determined. Then the equations set out above are used to determine the corrected transducer motion $\Delta X$ in the azimuthal direction. Next, $\Delta \theta'$ is corrected by the factor $\Delta X/\Delta X'$ to form $\Delta \theta$, which is free of motion distortion. The acquired image $I_1'$ is then corrected by $\Delta X/\Delta X'$ to correct for azimuthal transducer motion. Then $\Delta X$ and $\Delta \theta$ are used in the 3-D registration. Further details regarding the correction of images for azimuthal transducer motion are provided in co-pending U.S. Pat. Ser. No. 09/384,707, assigned to the assignee of the present invention and hereby incorporated by reference in its entirety.

C. Alternatives

The transducer motion compensation formulas presented above should be understood as a first order approximation which recovers the true motion in three orthogonal directions and associated rotations independently. In an alternate embodiment, the recovery formula can be derived with greater accuracy by solving the appropriate equations of motion. For example, we know the three translations and rotations obtained for a given image frame ($\Delta X'$, $\Delta Y'$, $\Delta Z'$, $\alpha'$, $\beta'$, $\gamma'$). These acquired variables are functions of the true translation and rotation ($\Delta X$, $\Delta Y$, $\Delta Z$, $\alpha$, $\beta$, $\gamma$) and the physical image width W. Six equations of motion can be listed and simultaneously solved to obtain $\Delta X$, $\Delta Y$, $\Delta Z$, $\alpha$, $\beta$, $\gamma$. It should be understood that any formula or computational approach that performs transducer motion correction and is consistent in first order to the formulas presented above is intended to be encompassed within the scope of this invention.

Many other alternatives are possible to the examples described above. For example, the spatial coordinates of individual frames can be measured in absolute space relative to a position sensor for the transducer probe or in tissue space relative to the tissue being imaged. As pointed out above, in some applications there is no need to correct the azimuthal transducer motion distortion, and the elevational transducer motion correction described above can be made as a function of scan line number, azimuthal pixel coordinate, or azimuthal pixel coordinate in combination with range pixel coordinate. If azimuthal transducer motion corrections are made, they can be made at any desired point in the image processing.

The foregoing detailed description has been intended by way of illustration and not limitation. It is only the following claims, including all equivalents, that are intended to define the scope of this invention.

What is claimed is:

1. A method for generating spatial coordinates of a medical diagnostic ultrasound image, said method comprising the following acts:

(a) determining motion in an elevation direction of a transducer that acquired the image; and then (b) determining elevational positions of a plurality of portions of the image as a function of (1) transducer motion in the elevation direction and (2) azimuthal positions of the respective portions of the image.

2. A method for correcting spatial coordinates of a medical diagnostic ultrasound image characterized by an elevational position, said method comprising the following acts:

(a) determining transducer motion in an elevational direction; and then (b) correcting elevational positions of a plurality of portions of the image as a function of (1) the transducer motion as determined in (a), and (2) azimuthal positions of the respective portions of the image.

3. The method of claim 1 or 2 further comprising the acts of:

(c) determining motion in an azimuthal direction of the transducer; and (d) correcting at least a portion of the image for azimuthal transducer motion distortion.

4. The method of claim 1 or 2 further comprising the acts of:

(e) determining in-plane rotation of the transducer; and (f) correcting at least a portion of the image for transducer rotation distortion.

5. The method of claim 1 or 2 further comprising the act of:

(g) registering the image in a 3-D spatial model using the elevational positions of (b).

* * * * *

UNITED STATES PATENT AND TRADEMARK OFFICE
CERTIFICATE OF CORRECTION

PATENT NO. : 6,254,539 B1
DATED : July 3, 2001
INVENTOR(S) : Linyong Pang et al.

It is certified that error appears in the above-identified patent and that said Letters Patent is hereby corrected as shown below:

Column 8,
Line 2, delete "AY" and substitute -- $\Delta Y$ -- in its place.
Line 45, delete "$I_1$'is" and substitute -- $I_1'$ is -- in its place.
Line 46, delete "$\Delta X/\Delta X$ '" and substitute -- $\Delta X/\Delta X'$ -- in its place.

Signed and Sealed this

Twenty-second Day of October, 2002

Attest:

JAMES E. ROGAN
Attesting Officer      Director of the United States Patent and Trademark Office